United States Patent [19]

Tomsovic, Jr.

[11] Patent Number: 4,767,487
[45] Date of Patent: Aug. 30, 1988

[54] METHOD FOR REPOSITIONING DISCRETE ARTICLES

[75] Inventor: James E. Tomsovic, Jr., Neenah, Wis.

[73] Assignee: Kimberly-Clark Corporation, Neenah, Wis.

[21] Appl. No.: 83,493

[22] Filed: Aug. 10, 1987

Related U.S. Application Data

[62] Division of Ser. No. 788,898, Oct. 18, 1985, Pat. No. 4,726,876.

[51] Int. Cl.$^4$ ............................................. B65G 47/31
[52] U.S. Cl. ..................... 156/256; 156/552; 156/556; 156/567; 156/568; 156/571; 198/459; 198/461; 198/476.1
[58] Field of Search ............... 156/164, 256, 519, 521, 156/567, 568, 571, 572, 522; 198/374, 379, 408, 415, 461, 468.4, 476.1, 459

[56] References Cited

U.S. PATENT DOCUMENTS

| | | | |
|---|---|---|---|
| 1,621,301 | 3/1927 | Wright | 198/476.1 |
| 3,374,752 | 3/1968 | Shirozu | 198/406 |
| 3,386,558 | 6/1968 | Benatar | 198/25 |
| 3,494,001 | 2/1970 | Banks | 198/34 |
| 3,827,545 | 8/1974 | Buhayar | 198/34 |
| 3,834,522 | 9/1974 | Jackson | 198/210 |
| 3,847,273 | 11/1974 | Buhayar | 198/236 |
| 3,887,065 | 6/1975 | Verjux | 198/280 |
| 4,021,293 | 5/1977 | Total | 156/568 |
| 4,164,996 | 8/1979 | Tomlinson | 198/415 |
| 4,394,898 | 7/1983 | Campbell | 198/374 |
| 4,471,865 | 9/1984 | Johnson | 198/408 |
| 4,506,779 | 3/1985 | Seragnoli | 198/461 |
| 4,578,133 | 3/1986 | Oshefsky et al. | 156/164 |
| 4,589,945 | 5/1986 | Polit | 156/521 |

FOREIGN PATENT DOCUMENTS 1113360 10/1954 France .
8020378 3/1982 France .
54-39121 10/1980 Japan .

Primary Examiner—Caleb Weston
Attorney, Agent, or Firm—Douglas L. Miller

[57] ABSTRACT

Apparatus for changing the spacing between articles of a moving array of discrete articles includes transfer means mounted for orbiting along a closed orbital path passing through a receiving zone and a discharge zone. The orbital radius of the transfer means is adjustable to provide an orbital radius in the discharge zone which is different from that in the receiving zone. The transfer means are maintained in fixed, equal angular distances between them along the orbital path whereby the orbital path distance between adjacent transfer means is different in the discharge zone from that in the receiving zone thereby resulting in a different spacing between adjacent articles in the discharge zone from that in the receiving zone. Two or more orbital spacer means may be utilized in tandem to provide the change in spacing in stages. A method of changing the spacing between discrete articles of an array of articles is disclosed and include moving the articles along a closed, non-circular orbital path between a receiving zone and a discharge zone and maintaining different orbital radii in the receiving and discharge zones whereby the orbital path distance between articles is changed between the receiving and discharge zones.

7 Claims, 3 Drawing Sheets

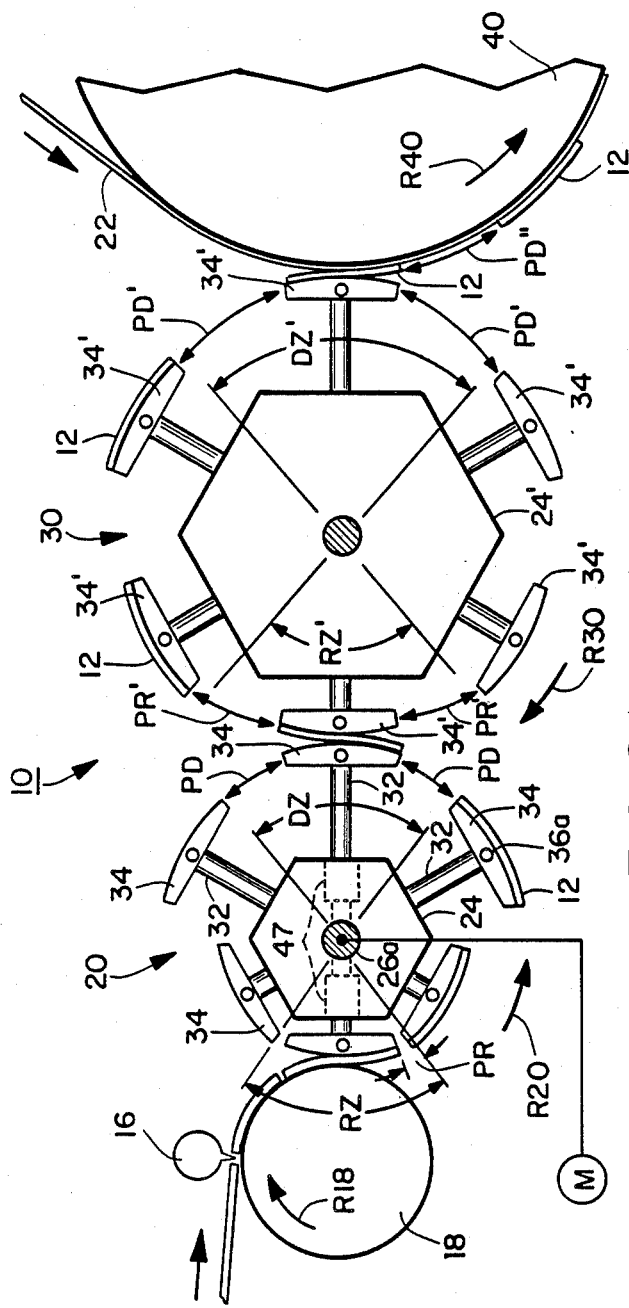
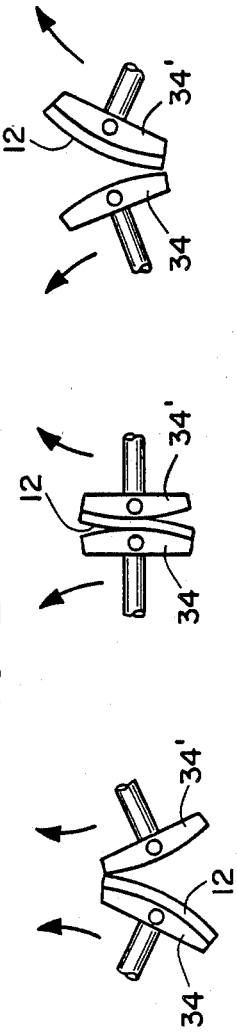
FIG. 2
FIG. 2A
FIG. 2B
FIG. 2C

METHOD FOR REPOSITIONING DISCRETE ARTICLES

This is a divisional of co-pending application Ser. No. 06/788,898 filed on Oct. 18, 1985 now Pat. No. 4,726,876.

BACKGROUND OF THE INVENTION

1. Field of the invention

The present invention is concerned with a method and apparatus for repositioning discrete articles such as segments cut transversely from a continuous moving web of material. For example, the present invention has utility with respect to repositioning discrete abutting segments of an absorbent material cut from a continuously moving web of the material, to form a spaced-apart array upon a continuously moving web of substrate material. Such technique may be utilized in the manufacture of disposable diapers, training pants and incontinence control garments generally.

Articles such as disposable diapers are generally made with a liquid-impervious backing sheet on which absorbent pads are positioned and covered by a liquid-pervious topsheet, the resulting composite material being cut into discrete articles. In many cases it is desired to place the discrete absorbent pads in a spaced-apart location onto the liquid-impervious backing sheet (or onto the liquid-pervious front sheet), which serves as the substrate upon which the absorbent pads are placed. However, the discrete absorbent pads are usually cut from a continuously moving web of the absorbent material or material formed in place, which produces a moving array of pads in an abutting relationship. Consequently, a means for placing the discrete absorbent pads onto the substrate web with a selected spacing between adjacent webs is required. In other applications, it may be desired to reverse the procedure, i.e., to place individual ones of an array of spaced-apart articles into continuous abutting array or to change the spacing between adjacent articles from one distance to another distance.

2. Description Of Related Art

U.S. Pat. No. 3,386,558 discloses a feeder mechanism in which a device having fixed, radially extending arms is cam driven so that, as the device rotates, pneumatic suction cup gripping means at the ends of the arms travel along the path indicated in FIG. 2 for removing folded carton blanks 5 from a hopper 3 and depositing them atop stacked containers C moving along a conveyor belt 6. Rotationally eccentric movement is provided to the means 19 which carries the fixed arms thereon.

U.S. Pat. No. 3,834,522 shows a transfer machine comprising a turret having a plurality of radially translatable carriages mounted thereon, which carriages are fitted with a suction cup 46 (FIG. 2) for gripping a container. A cam track (85 in FIG. 4) moves the carriages radially outwardly during rotation so as to enable the suction cups to grip the container at the unloading station, then retracts radially inwardly for transporting the container, and then moves radially outwardly to feed the container into the stacking device. The turret provides for intermittent movement between the stations to allow sufficient dwell time for the freshly printed containers to dry.

U.S. Pat. No. 3,494,001, shows apparatus and method for making sanitary napkins and discloses at column 10, line 58 et seq and FIGS. 11 and 12, the use of paired rolls operating at different peripheral speeds so as to separate individual articles 116 passing therethrough.

U.S. Pat. No. 3,827,545 concerns method and apparatus for changing the spacing between discrete, flexible web products and utilizes, as illustrated in FIGS. 1 and 3a–3d, a variable-speed pinch roll 14 positioned between respective conveyor belts 12 and 16, which operate at different speeds. The peripheral speed of the rolls comprising pinch roll 14 is varied between the respective speeds of conveyor belts 12 and 16. The patentee refers to positive control being exercised on the transferred object (column 7, lines 19–20).

U.S. Pat. No. 3,847,273 discloses a transfer means comprising a rotating drum having radially extending arms which carry gripper means for orbiting about the drum axis of rotation, as illustrated in FIG. 1. The radial arms 26 are constant radius arms which rotate about their own axes to pivotably turn articles 12. Consequently, changes in spacing between adjacent articles are effected only to the extent of the difference between the length and width of the individual transferred articles.

U.S. Pat. No. 4,394,898 discloses method and apparatus for providing balanced stacks of diapers by turning alternately dispensed diapers 90° to the right and the remaining alternately dispensed diapers 90° to the left, so that 180° rotation is provided between adjacent diapers. A rotating drum having fixed, radially extending arms carrying pads which engage the dispensed diapers is provided. The arms rotate about their own axes.

French patent No. 2,490,601 shows a rotating turret 15 equipped with fixed diameter radial arm and adapted to remove individual articles from a stack 5a thereof to place them onto a conveyor belt 1.

U.S. Pat. No. 3,374,752 shows a transplanter for handling paper cylinders containing seedlings which are transferred from a conveyor belt 10 to members 22 mounted for rotation so as to deposit the seedling cylinder into a furrow opened by a plow blade ("opener") 3. The members 22 remain at a constant radial distance from the axis of rotation.

Various types of transfer mechanisms are exemplified in U.S. Pat. Nos. 3,887,605; 4,164,996 and 4,471,865 and in French patent No. 1,113,360 and Japanese patent publication No. 55135026.

Copending patent application Ser. No. 673,064, filed Nov. 19, 1984 and entitled "Method And Apparatus For Applying Discrete Strips To A Web Of Material" discloses radially extending and retracting shoes employed to transfer segments of elastic strips dispensed at one linear speed onto a continuous web traveling at a different linear speed. A change in the orbital radius of the shoes during their traverse of the orbital path changes the orbital path speed of the shoe to accommodate the different linear speeds.

SUMMARY OF THE INVENTION

In accordance with the present invention there is provided apparatus for changing the spacing between articles of a moving array of discrete articles, the apparatus comprising at least one spacer means comprising: an orbital drive means having transfer means mounted thereon, for example, on radially translatable supports carried by the orbital drive means, for orbiting of the transfer means along a closed orbital path passing through a receiving zone and a discharge zone; gripper means on the transfer means effective to grasp discrete articles in the receiving zone and to release the discrete articles in the discharge zone; and radius-adjusting means operatively connected to the transfer means to selectively adjust the orbital radius thereof between a receiving zone radius and a discharge zone radius which is different from the receiving zone radius, whereby the closed orbital path is a non-circular orbital path, and the orbital path distance between adjacent transfer means in the receiving zone is different from the orbital path distance between adjacent transfer means in the discharge zone.

In one aspect of the invention, the apparatus comprises two or more of the spacer means respectively positioned with the discharge zone of the relatively upstream spacer means being located proximate to the receiving zone of the adjacent downstream spacer means.

In another aspect of the invention, the radius-adjusting means is dimensioned and configured to adjust the orbital radius to provide a discharge zone radius which is larger than the receiving zone radius, whereby the orbital path distance between adjacent transfer means of a given spacer means is greater in its discharge zone than in its receiving zone. When two or more spacer means are used, the orbital path distance between adjacent transfer means in the final (downstream) spacer means may be greater than that in the initial (upstream) spacer means.

Other aspects of the invention provide for the inclusion of (a) inbound article conveyor means disposed relative to the spacer means to supply a moving array of discrete articles to the receiving zone thereof, and (b) outbound article conveyor means disposed relative to the spacer means to receive a moving array of discrete articles from the discharge zone thereof, provided, that when the apparatus comprises two or more spacer means, the inbound article conveyor supplies the receiving zone of the initial upstream spacer means and the outbound article conveyor services the discharge zone of the last downstream spacer means.

Still other aspects of the invention provide one or more of the following features: the inbound and outbound conveyor means are each continuously moving conveyor means; the transfer means have article-retaining surfaces which are convex in the orbital path direction; the transfer means are mounted on the orbital drive means at identical fixed angular distances one from the other along the orbital path; and the orbital drive means is a continuous drive means for continuously orbiting the transfer means along the orbital path.

In another aspect of the invention, the orbital drive means and the radius adjusting means are dimensioned and configured so that the linear velocity of the inbound conveyor means is substantially equal to that of the transfer means in the receiving zone of the spacer means which is supplied by the inbound conveyor means. Similarly, the linear velocity of the outbound conveyor means is substantially equal to that of the transfer means in the discharge zone of the spacer means which is serviced by the outbound article conveyor means. In those cases in which the apparatus comprises two or more spacer means, the linear velocity of transfer means in the discharge zone of an upstream spacer means is substantially equal to the linear velocity of transfer means in the receiving zone of the adjacent downstream spacer means.

Yet another aspect of the invention provides that the transfer means have respective leading sections and trailing sections and the gripper means include first activatable gripper means disposed in the leading sections and second activatable gripper means disposed in the trailing sections, the spacer means further including gripper control means to selectively activate and inactivate the first and second gripper means independently of each other. For example, the gripper control means may be configured to inactivate in the discharge zone the first gripper means before the second gripper means of a given transfer means, whereby the portion of an article held by the first gripper means of a transfer means is released in the discharge zone while the second gripper means of the same transfer means retains its grip on another portion of the same article.

The invention also provides for two or more of the spacer means to be respectively positioned with the discharge zone of relatively upstream spacer means being located proximate to the receiving zone of the adjacent downstream spacer means, the respective spacer means being configured and dimensioned to bring the orbital paths of their respective transfer means into leading section-to-leading section synchronization.

The present invention also provides a method for changing the spacing between articles of a moving array of discrete articles, the method comprising the steps of: moving the article along at least one closed, non-circular orbital path passing through (i) a receiving zone in which the articles are maintained in a receiving zone orbital radius and (ii) a discharge zone in which the articles are maintained in a discharge zone orbital radius which is different from the receiving zone orbital radius, with the orbital path distance between adjacent articles in the receiving zone being maintained to be different from the orbital path distance between adjacent articles in the discharge zone; in the receiving zone, transferring discrete articles from a first array of inbound discrete articles to the orbital path and, in the discharge zone, transferring the discrete articles from the orbital path to a second array of outbound articles, whereby the linear spacing between adjacent discrete articles deposited in the second array of articles is different from the linear spacing between adjacent discrete articles in the first array of articles.

The method aspects of the invention may also include one or more of the following steps or sequence of steps: maintaining a discharge zone orbital radius which is larger than the receiving zone orbital radius and maintaining a fixed angular distance along the orbital path between adjacent transfer means whereby the orbital path distance between adjacent articles is greater in the discharge zone than in the receiving zone; continuously moving the articles along the orbital path; continuously moving both the first and second array of discrete articles; and transferring the discrete articles from the inbound array to the outbound arraray along two or more sequentially positioned orbital paths.

Other aspects of the present invention include moving the articles along the at least one orbital path by use of transfer means having activatable grippers thereon, and comprising the additional steps of gripping the articles in the receiving zone by activating the gripper means and releasing the articles in the discharge zone by therein inactivating the gripper means.

Yet another aspect of the method of the present invention includes inactivating the gripper means of a given transfer means in at least two stages to release a first, leading part of a given article while retaining its grip on a second, trailing part of the same article until the first part of the article is transferred.

Other aspects of the invention will be apparent from the following description of preferred embodiments thereof.

BRIEF DESCRIPTION OF THE DRAWINGS

FIG. 2 is a schematic side view in elevation of the apparatus of FIG. 1;

FIGS. 2A, 2B and 2C show sequential relative operating positions of a pair of synchronized transfer means of the two spacer means of the apparatus of FIG. 2.

DETAILED DESCRIPTION OF THE PREFERRED EMBODIMENTS

Figure 1:
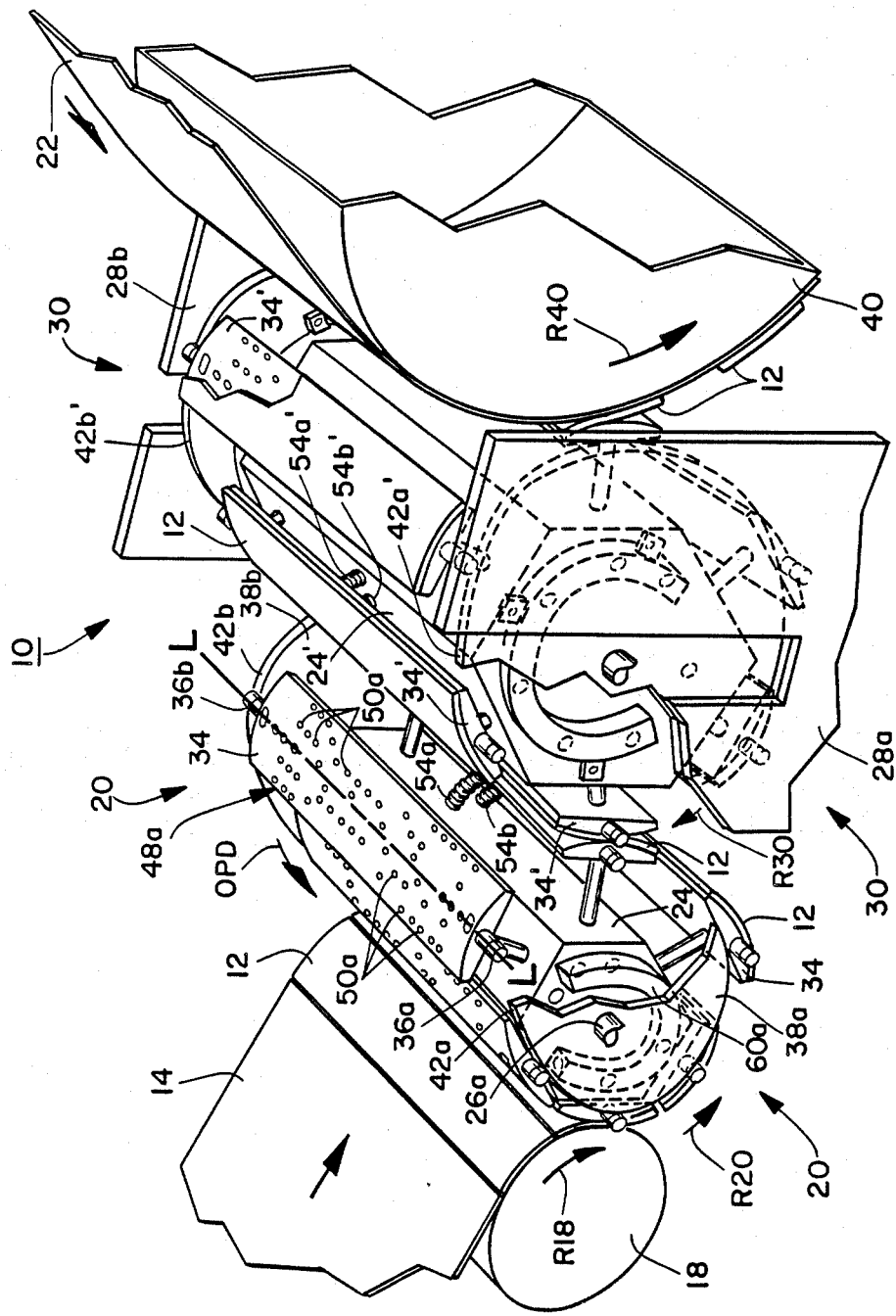
FIG. 1 is a perspective view, with some parts broken away and some omitted for clarity of illustration, of one embodiment of an apparatus of the present invention.

Referring now to FIGS. 1 and 2 there is shown an apparatus generally indicated at 10 for changing the spacing between articles 12 of a moving array of discrete articles cut from a continuous web 14 travelling in the direction indicated by the arrow associated therewith. In the embodiment illustrated in FIGS. 1 and 2, feed drum 18 comprises an inbound article conveyor means which supplies a moving array of discrete articles 12 to a first spacer means 20 from whence the articles 12 are conveyed to a second, larger diameter spacer means 30, thence to discharge drum 40 which, in the illustrated embodiment, provides an outbound article conveyor means positioned relative to the second spacer means 30 to receive a moving array of the discrete articles 12 from the discharge zone (DZ' in FIG. 2) thereof. The respective directions of rotations of feed drum 18, first spacer means 20, second spacer means 30 and discharge drum 40 are indicated in FIGS. 1 and 2 by the arrows $R_{18}$, $R_{20}$, $R_{30}$ and $R_{40}$ respectively associated therewith. Receiving zone RZ and discharge zone DZ of first spacer means 20 are defined by respective segments of the orbital path travelled by transfer means 34 of spacer means 20. Similarly, receiving zone RZ' and discharge zone DZ' of second spacer means 30 are defined by respective segments of the orbital path travelled by transfer means 34' of spacer means 30. A continuous travelling substrate web 22 is fed, in the direction indicated by the unnumbered arrow associated therewith, about discharge drum 40 for placement thereon of spaced-apart discrete articles 12. It will be apparent that substrate web 22 may, in certain embodiments of the invention, be omitted and the discrete articles 12 placed in spaced-apart location directly upon discharge drum 40 for subsequent processing. However, in the illustrated embodiment the spaced-apart articles 12 are placed upon substrate web 22 at a desired spacing in the direction of travel between adjacent articles 12. The articles 12 may optionally be adhered to substrate web 22 by means of an adhesive applied in a selected pattern to the surface of substrate web 22 or by any other suitable means.

First spacer means 20 comprises (FIGS. 1 and 2) a drum 24 mounted for rotation by a pair of stub shafts, only one of which (stub shaft 26a) is visible in the drawings. Stub shaft 26a and its counterpart (which is coaxially aligned with stub shaft 26a and located at the opposite lateral end of drum 24) serve to mount drum 24 between a pair of spaced-apart stanchions which, for clarity of illustration, are not shown in FIG. 1 but which are substantially the same as stanchions 28a, 28b which serve to support drum 24' of second spacer means 30 in the same manner as drum 24 is supported by its associated stanchions. As best seen in FIG. 2, three pairs of radially translatable support means 32 extend through opposite circumferential faces of drum 24 and support at their respective opposite ends respective ones of transfer means comprising, in the illustrated embodiment transfer shoes 34. Transfer shoes 34 are affixed by any suitable means such as bolts or the like to respective opposite ends of their associated support means 32 which, in the illustrated embodiment of FIG. 2, comprise rigid rods mounted within slide bearings 47 for sliding movement relative to drum 24. Obviously, other structures could be employed such as mounting each transfer shoe 34 on its own radially translatable support means, such as a telescoping tube arrangement. Transfer shoes 34 may be rigidly mounted upon the radially translatable support means 32 or may be mounted for pivoting or rocking movement relative thereto in the direction of travel to facilitate smooth transfer of articles 12. At the respective opposite lateral ends of each transfer shoe 34 there is provided a cam follower 36a, 36b. As shown in FIG. 1, a pair of oval-shaped cam plates 38a, 38b are mounted in facing relationship on the respective inside faces of stanchions 28a, 28b and the peripheral edges of cam plates 38a, 38b provide respective peripheral edge cam tracks 42a, 42b (FIG. 1) along which cam followers 36a, 36b respectively travel. The respective cam tracks 42a42b are mirror images of each other and are aligned with each other so that the paired cam tracks control radial movement of transfer shoes 34 as described below. Stub shaft 26a and its counterpart respectively pass through suitable openings in cam plate 38a, 38b and are journaled in suitable bearings (not shown) mounted on the stanchions supporting drum 24.

A suitable drive means such as a motor M schematically indicated in FIG. 2 is operatively connected through suitable gearing (not shown) to one or both of stub shafts 26a and its counterpart for rotation of drum 24 about its axis of rotation which is coincident with the longitudinal axes of stub shafts 26a and its counterpart. (A similar drive means, not illustrated, may be provided for drums 24', 18 and 40.) Cam tracks 42a and 42b are eccentric relative to the axis of rotation of drum 24 so that as the latter rotates to orbit transfer shoes 34, each connected pair of transfer shoes 34 is radially translated by virtue of cam followers 36a, 36b following their associated cam tracks 42a, 42b. In this way, each of the orbiting transfer shoes 34 orbits along a non-circular closed orbital path passing through a receiving zone RZ (FIG. 2) in which the transfer shoes 34 have a relatively small orbital radius and a discharge zone DZ in which the transfer shoes 34 have a relatively large orbital radius. The cam tracks may have any suitable eccentric configuration so as to provide a desired different orbital radius in each of the receiving zone RZ and discharge zone DZ of spacer means 20 so as to provide between adjacent transfer shoes 34 a desired orbital path distance PR in receiving zone RZ and a desired (larger, in the illustrated embodiment) orbital path distance PD in discharge zone DZ. As illustrated, support means 32 are radially translatable but angularly fixed relative to each other so that there is an equal, fixed angular distance between adjacent support means 32 and the transfer shoes 34 carried thereon. The arrangement illustrated in FIG. 2 provides 60° of angular distance between the respective longitudinal axes of each of the six protruding support means 32.

The construction of second spacer means 30 may be similar or identical to that of first spacer means 20 except that second spacer means 30 is preferably of larger diameter than first spacer means 20 so that the respective orbital radii and orbital path distances between the transfer shoes 34' are larger than those of transfer shoes 34. Accordingly, it is not necessary to repeat in detail a description of second spacer means 30 except to note that the various components thereof which correspond to those of first spacer means 20 are numbered identically thereto, except for the addition of a prime notation. It will be noted from FIG. 2 that the receiving zone RZ' of second spacer means 30 is disposed adjacent the discharge zone DZ of first spacer means 20. First spacer means 20 is thus considered the "upstream" spacer means and second spacer means 30 the "downstream" spacer means, such designation being applied with regard to movement of the articles 12. The orbital path distance PR' between adjacent transfer shoes 34' of second spacer means 30 in receiving zone RZ' thereof is greater than the orbital path distance PD between transfer shoes 34 in discharge zone DZ of second spacer means 20. The orbital path distance PD' between adjacent transfer shoes 34' of second spacer means 30 in the discharge zone DZ' thereof is still greater and therefore substantially greater than the corresponding distance PD in the discharge zone DZ of first spacer means 20. The orbital path distance PR is very small or may even be zero, since the transfer shoes 34 may be in substantially abutting contact in receiving zone RZ of first spacer means 20 in order to receive the abutting articles 12 cut from web 14. Utilization of the two spacer means 20 and 30 provides a staged increase in the orbital path distances from PR to PD' in order to avoid the necessity for excessively long radial distances to be travelled by a given transfer shoe 34 within the time allowed by one-half of a complete rotation of its associated drum. In some cases, a single spacer means will suffice to carry out the change in spacing and in other cases more than two spacer means may be used in tandem, depending on the required change in spacing distances and speed of operation. In most cases, it is desired or necessary that the apparatus and its operation be arranged so that the linear velocities of a transfer shoe and the member transferring an article to, or receiving an article from, the transfer shoe are substantially the same.

While a given transfer shoe 34 of spacer means 20 is within receiving zone RZ, gripping means thereon are actuated, as described in more detail below, to grip and transport a discrete article 12 cut from travelling web 14. The orbital radius of the transfer shoe 34 carrying a given article 12 is increased as the transfer shoe 34 rotates from receiving zone RZ into discharge zone DZ. In discharge zone DZ the transfer shoe 34 having the article 12 thereon is brought into facing relationship with a corresponding transfer shoe 34' of second transfer means 30, as indicated by the sequence shown in FIGS. 2A and 2B. Transfer shoes 34, 34' of FIGS. 2A–2C are synchronized to meet in a leading edge-to-leading edge facing relationship (FIG. 2A) and to travel synchronously through center-to-center (FIG. 2B) and trailing edge-to-trailing edge (FIG. 2C) facing relationship. Thus, reference to respective ones of transfer shoes 34 of spacer means 20 and transfer shoes 34' of spacer means 30 being "synchronized" refers to at least sufficient facing relationship as illustrated in FIGS. 2A–2C to enable transfer of an article from one shoe to the other. At a position intermediate those shown in FIGS. 2A and 2B the gripping means associated with transfer shoe 34 is at least partially released so that article 12 may be grasped by the activated gripping means on transfer shoe 34' for transfer thereto as indicated in FIG. 2C. Transfer shoes 34' of second transfer means 30 receive the transferred articles 12 and orbit from receiving zone RZ' of second transfer means 30 to discharge zone DZ' thereof to deposit the articles 12 upon the travelling substrate web 22 in discharge zone DZ'. While traversing their respective orbital path segments shown in FIGS. 2A–2C, transfer shoes 34 and 34' preferably have the same or nearly the same linear velocities in order to facilitate transfer of articles 12. This can readily be provided by selection of orbital velocity and orbital radius of the transfer shoes 34, 34' while passing through, respectively, discharge zone DZ and receiving zone RZ'. Similarly, linear velocities of the surfaces of feed drum 18 and discharge drum 40 are preferably appropriately controlled to substantially equal those of, respectively, transfer shoes 34 in receiving zone RZ and transfer shoes 34' in discharge zone DZ'.

The respective gripping means holding articles 12 to transfer shoes 34' are inactivated in discharge zone DZ' whereby articles 12 are released and deposited upon substrate 22 (or, in the absence of a substrate web 22, directly onto discharge drum 40.) Adhesive may be applied to articles 12 and/or in an appropriate pattern onto substrate web 22 in order to adhere article 12 firmly to substrate web 22. As shown in FIG. 2, the travel path distance between adjacent articles 12 deposited upon substrate web 22 is indicated as a distance PD" because this distance may be different from the orbital path distance PD' between adjacent transfer shoes 34' in discharge zone DZ'. However, in the illustrated embodiment the periphery of drum 40 has substantially the same linear velocity as transfer shoes 34' and articles 12 are substantially as long (in the direction of travel) as the transfer shoes 34' carrying them so the distance PD' is equal to the distance PD". Obviously, if articles 12 were shorter than the (leading edge-to-trailing edge) length of transfer shoes 34' and centered thereon, the travel path distance between adjacent articles 12 would be PD' plus the difference in length between articles 12 and their associated transfer shoes 34', assuming equal peripheral speeds of drum 40 and shoes 34'.

Figure 3:
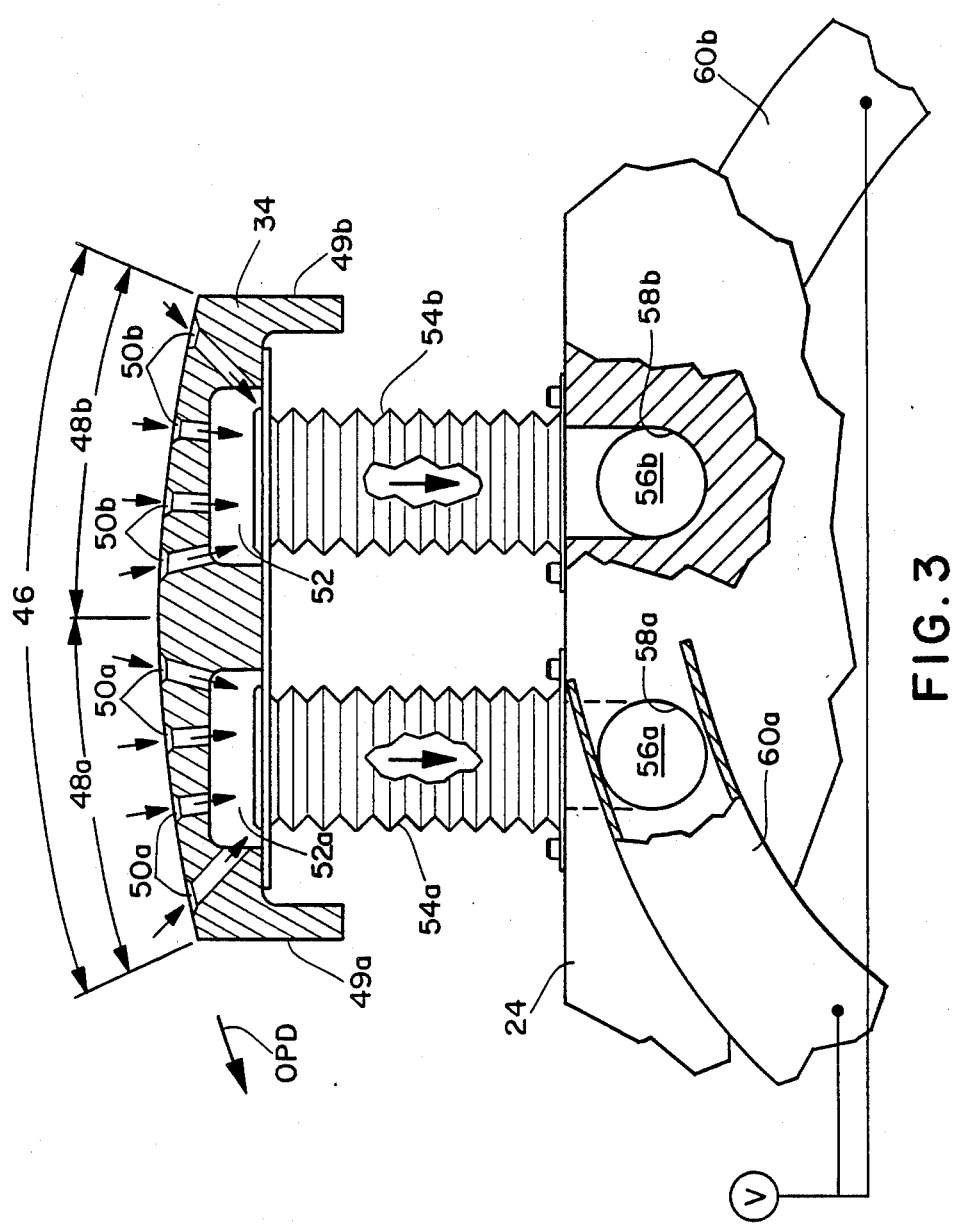
FIG. 3 is a partial cross-sectional view on an enlarged scale of a typical transfer shoe and part of the drum of the smaller of the two spacer means of the device of FIG. 1, the cross sections being taken perpendicularly to the axis of rotation of the drum.

Referring now to FIGS. 1 and 3, the illustrated embodiment of the transfer means comprises a typical transfer shoe 34 of spacer means 20 having an article-retaining surface 46 which, as best seen in FIG. 3, is convex in the orbital path direction, i.e., is convex in the direction of movement of transfer shoe 34 as it traverses its closed orbital path. (This orbital path direction of movement is indicated by the arrow OPD in FIGS. 1 and 3.) Article-retaining surface 46 has a leading section 48a thereof comprising that portion of article-retaining surface 46 which is between the longitudinal axis L—L (FIG. 1) and leading edge 49a (FIG. 3) of transfer shoe 34. The remainder of the article-retaining surface 46, between longitudinal axis L—L and trailing edge 49b, is considered to be the trailing section 48b of transfer shoe 34.

In the illustrated embodiment, the gripper means comprise ports of pneumatic lines through which a vacuum may be selectively imposed. Thus, ports 50a (FIGS. 1 and 3) comprise first activatable gripper means disposed within leading section 48a and connected in pneumatic flow communication with a transfer means manifold 52a (FIG. 3) which in turn is connected to a bellows conduit 54a which extends from transfer means manifold 52a to a drum conduit 56a, which terminates in a connector port 58a in a lateral side of drum 24 (FIGS. 1 and 3).

Referring jointly to FIGS. 1 and 3, a vacuum manifold 60a is connected to a source of vacuum V (schematically illustrated in FIG. 3) to continuously maintain a vacuum within vacuum manifold 60a (and vacuum manifold 60b as described below). As seen in FIG. 1, vacuum manifold 60a is in the shape of a segment of a circle so that as drum 24 rotates a connector port 58a associated with the activatable gripper means of the leading section 48a of a particular transfer shoe 34 will be in pneumatic flow communication with vacuum manifold 60a for a portion only of one complete revolution of drum 24, and will be isolated from vacuum manifold 60a for the remaining portion of each revolution. Thus, vacuum may be imposed upon ports 50a of transfer shoes 34 for only a selected portion of each cycle of rotation by designing vacuum manifold 60a to encompass a selected segment of a complete circle. The interrupted segment of vacuum manifold 60a is positioned in alignment with a selected portion of the rotational path of drum 24. Thus, when connector port 58a illustrated in FIG. 1 is not aligned with vacuum manifold 60a it is exposed to the atmosphere and the ports 50a connected to the exposed connector ports 58a are not under vacuum. However, when a given connector port 58a is aligned with vacuum manifold 60a a vacuum is pulled thereon and thereby also upon the ports 50a associated therewith so that a gripping action is imposed on that portion of the article 12 which overlies ports 50a.

Still referring to FIGS. 1 and 3, the vacuum connections for the ports 50b located in the trailing section 48b of transfer shoe 34 are similar or identical to those for the ports 50a. That is, ports 50b are in pneumatic flow communication with the transfer means manifold 52 which in turn is connected to a bellows conduit 54b, thence via a drum conduit 56b to a connector port 58b in the lateral end of drum 24 which is opposite to that in which the connector ports 58a are disposed. A vacuum manifold 60b (FIG. 3) of similar construction to vacuum manifold 60a is connected to the source of vacuum V as schematically indicated in FIG. 3 so that when connector ports 58b are aligned with vacuum manifold 60b, a vacuum is imposed upon ports 50b as described above. Vacuum manifolds 60b (not visible in FIG. 1) are, like vacuum manifolds 60a, of a construction which defines an arcuate segment of a circle, less than a complete circle, so that for a selected portion of its rotational path a given connector port 58b is exposed to the atmosphere and not aligned with vacuum manifold 60b. The interrupted segment of vacuum manifold 60b is, however, positioned out of register with the interrupted portion of vacuum manifold 60a. In other words, as viewed along the longitudinal axis of stub shafts 26a and its counterpart stub shaft (FIG. 1) the arcuate segments of vacuum manifolds 60a and 60b are out of alignment one with the other along the rotational path of drum 24 so that the periods of interruption of vacuum on, respectively, ports 50a and 50b are out of synchronization. In the illustrated embodiment, a connector port 58a associated with the leading section 48a of a given transfer shoe 34 will clear its associated vacuum manifold 60a before the connector port 58b associated with the trailing section 48b of the same transfer shoe 34 clears its vacuum manifold 60b. In this manner, as illustrated in FIG. 2B, the gripping action imposed by ports 50a of a given transfer shoe 34 on the article 12 carried thereon is released while the gripping action maintained on the same article 12 by the ports 50b of the same transfer shoe 34 is maintained. This maintains control of each article 12 by transfer shoe 34 while the gripping force imposed by the leading section of transfer shoe 34' is being established. Only then is the gripping force imposed by the trailing section 48b of transfer shoe 34 released to complete the transfer from transfer shoe 34 to transfer shoe 34', as illustrated in FIG. 2C. In this manner, positive control is maintained over the articles 12 at all times during the transfer process since there is no time at which the articles 12 are free of the gripping action provided by one or the other of the transfer shoes 34, 34'.

Generally, rotation of spacer means 20 and 30 and of drums 18 and 40 is preferably continuous rather than intermittent, and more preferably is continuous and of constant rotational velocity to avoid the necessity of accelerating and decelerating the apparatus. Thus, the spacer means, or at least the drums 24 and 24' thereof, preferably continuously rotate at constant rotational velocities. The linear velocity of the transfer shoes 34 and 34' along their respective orbital paths will of course vary directly with their orbital radius. Drums 18 and 40 or equivalent conveyor belts or the like will likewise preferably have continuous, constant linear velocities. As noted above, dimensions and rotational speeds of the components of the apparatus will preferably be designed to match linear velocities of receiving and discharging members in their respective receiving and discharge zones.

Those skilled in the art will recognize that numerous details of construction embodying well-known machine design expedients have been eliminated or not described for clarity and simplicity of illustration. For example, a wear plate would normally be provided between drum 24 and stationary vacuum manifolds 60a and 60b. It will further be appreciated that the apparatus of the invention can utilize one or, alternatively, can utilize two, three or more spacer means in tandem, depending on the desired difference in spacing between received and discharged articles and operating speeds. It will further be appreciated that the illustrated direction of rotations of the two illustrated spacer means 20 and 30 and of drums 18 and 40 could be reversed so that articles received in an array of spaced-apart articles could be placed in closer proximity to each other, including abutting or even overlapping relationship to each other. It will further be appreciated that one or both of the feed drum 18 and discharge drum 40 could be replaced by any other suitable conveyor means, such as an endless belt or the like.

While the invention has been described in detail with respect to specific preferred embodiments thereof, it will be appreciated by those skilled in the art that numerous alterations and embodiments thereto may readily be conceived upon a reading and understanding of the foregoing and that such alterations and embodiments will nonetheless lie within the scope of the invention and the appended claims.

What is claimed is:

1. A method for changing the spacing between articles of a moving array of discrete articles, comprising the following steps:

moving the articles along at least two sequentially positioned closed, non-circular orbital paths, each path passing through (i) a respective receiving zone in which the articles are maintained in the respective receiving zone orbital radius and (ii) a respective discharge zone in which the articles are maintained in the respective discharge zone orbital radius which is different from the receiving zone orbital radius, with the orbital path distance between adjacent articles in each receiving zone being different from the orbital path distance between adjacent articles in each respective discharge zone;

in the receiving zone of a first positioned closed, non-circular orbital path, transferring discrete articles from a first array of inbound discrete articles to the orbital path and, in the discharge zone of a last positioned closed, non-circular orbital path, transferring the discrete articles from the orbital path to a second array of outbound articles, whereby the linear spacing between adjacent discrete articles deposited in the second array of articles is different from the linear spacing between adjacent discrete articles in the first array of articles.

2. The method of claim 1 including maintaining a discharge zone orbital radius which is larger than the receiving zone orbital radius and maintaining a fixed angular distance along the orbital path between adjacent transfer means whereby the orbital path distance between adjacent articles is greater in the discharge zone than in the receiving zone of a given closed orbital path.

3. The method of claim 1 including transferring the discrete articles to the orbital path of the first positioned orbital path from an inbound conveyor means transporting the first array of discrete articles, and receiving the second array of discrete articles from the orbital path of the last positioned orbital path on an outbound conveyor means.

4. The method of claim 1 including continuously moving the articles along the orbital path.

5. The method of claim 4 including continuously moving both the first and second array of discrete articles.

6. The method of claim 1 including moving the articles along at least one of the orbital paths by use of transfer means having activatable grippers thereon, comprising the additional steps of gripping the articles in the receiving zone by activating the gripper means and releasing the articles in the discharge zone by therein inactivating the gripper means.

7. The method of claim 6 including inactivating the gripper means of a given transfer means in at least two stages to release a first, leading part of a given article while retaining its grip on a second, trailing part of the same article until the first part of the article is transferred.

* * * * *